United States Patent [19]

Mankoo

[11] Patent Number: 5,589,158
[45] Date of Patent: Dec. 31, 1996

[54] FLAVOR ENHANCER

[75] Inventor: Amrit S. Mankoo, New Hampton, N.Y.

[73] Assignee: Bush Boake Allen Inc., Montvale, N.J.

[21] Appl. No.: 340,930

[22] Filed: Nov. 17, 1994

[51] Int. Cl.$^6$ ..................................................... A61K 7/16
[52] U.S. Cl. ................................................................ 424/49
[58] Field of Search ................................................ 424/49

[56] References Cited

U.S. PATENT DOCUMENTS 4,608,193  8/1986  Sprecker ............................. 252/522 R

OTHER PUBLICATIONS

CA 108: 118752 1987.

Primary Examiner—Paul J. Killos
Attorney, Agent, or Firm—Beth Kovitz Fields; Charles A. Gaglia, Jr.; Wendy A. Choi

[57] ABSTRACT

A flavor enhancing composition including benzyl benzoate and neryl acetate is provided in accordance with the invention. The flavor enhancing composition can be provided in either solid, i.e. powder, or liquid form and is used to enhance the flavor of mints, gums, candy, oral hygiene products and the like.

13 Claims, No Drawings

FLAVOR ENHANCER

FIELD OF THE INVENTION

This invention relates generally to flavor enhancers and, in particular, to a flavor enhancer for enhancing the flavor of mints, gums, candy, oral hygiene products and the like.

BACKGROUND OF THE INVENTION

Flavor enhancing agents are commonly used to make products taste better. They are used in a wide variety of products including, for example, mints, gums, candy and oral hygiene products such as mouthwash, dental floss, dental grips and adhesives for dentures, toothpaste, and the like.

It is, therefore, desirable to provide new flavor enhancing compositions that can be used to enhance the flavor of all of these products.

SUMMARY OF THE INVENTION

Generally speaking, a flavor enhancing composition including benzyl benzoate and neryl acetate is provided in accordance with the invention. The flavor enhancing composition can be provided in either solid, i.e. powder, or liquid form and is used to enhance the flavor of mints, gums, candy, oral hygiene products and the like.

The invention accordingly comprises a composition of matter possessing the characteristics, properties, and the relation of components which will be exemplified in the composition hereinafter described, and the scope of the invention will be indicated in the claims.

DETAILED DESCRIPTION OF THE PREFERRED EMBODIMENTS

The flavor enhancing composition provided in accordance with the invention includes benzyl benzoate and neryl acetate. The composition can be provided in either solid, such as a spray dried powder, or liquid form. An alcoholic vehicle such as ethyl alcohol can be used when the composition is provided in liquid form. Other flavor enhancing components can also be used and the composition can be used to enhance the flavor of mints, gum, candy, oral hygiene products, and the like.

Benzyl benzoate has the structure:

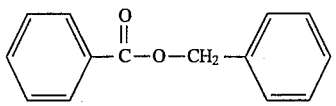

and can be used in an amount between about 30% and 90% by weight of the composition. The amount of benzyl benzoate used depends on whether the composition is provided in a solid, i.e. spray-dried powder, form or in a liquid vehicle. When the composition is provided in a solid form, generally the amount of benzyl benzoate will be near the high end of the range since there will be no solvent present. Conversely, when the composition is provided in a liquid form, the amount of benzyl benzoate will be closer to the low to mid-point of the range since it is necessary to account for the presence of a solvent.

Neryl acetate has the structural formula:

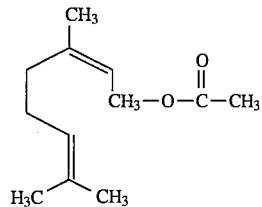

and can be used in an amount between about 3% and 15% by weight of the composition. In a preferred embodiment, the neryl acetate is used in an amount between about 5% and 10% by weight of the composition, and in a more preferred embodiment, the neryl acetate is used in an amount between about 7% and 7.5% by weight.

When the composition is provided in a solid form such as a spray dried powder, it is carried on a suitable carrier. Suitable carriers include, but are not limited to, maltodextrin, modified food starch, gum acacia, dextrin, corn syrup solids, and mixtures thereof.

When the composition is provided in a liquid form, a suitable vehicle such as an alcoholic solvent, an oil, or a hydrocolloid emulsion can be used. Suitable vehicles include, for example, ethyl alcohol, propylene glycol, glycerol, hydrogenated and/or non-hydrogenated oils, food starches, vegetable gums, and mixtures thereof. The vehicle can be used in an amount between about 10% and 90% by weight of the composition, preferably in an amount between about 60% and 65% by weight.

Other flavor enhancing agents can optionally be used in the composition of the invention. Suitable flavor enhancing agents include, for example, but are not limited to, citronellyl acetate, geranyl acetate, geranyl propionate, linalool, alpha-ionone, 2,2,6-tri-methyl-6-vinyl-tetrahydropyran, citronella oil, and mixtures thereof. The optional flavor enhancing agents can each be used in an amount between about 0.01% and 1% by weight of the composition.

The following Examples 1 and 2 show flavor enhancing compositions prepared in accordance with the invention. These examples are presented for purposes of illustration only and are not to be construed in a limiting sense.

EXAMPLE 1

Thirty (30) parts by weight benzyl benzoate, 7.5 parts by weight neryl acetate, 0.1 parts by weight 2,2,6-trimethyl-6-vinyltetrahydropyran, 0.1 parts by weight citronella oil, and 62.3 parts by weight of 190 proof undenatured ethyl alcohol were compounded and mixed well to provide a flavor enhancing composition in accordance with the invention.

EXAMPLE 2

Sixty-two and three-tenths (62.3) parts by weight of 190 proof undenatured ethyl alcohol, 30 parts by weight benzyl benzoate, 7 parts by weight neryl acetate, 0.1 parts by weight citronellyl acetate, 0.1 parts by weight geranyl acetate, 0.05 parts by weight geranyl propionate, 0.02 parts by weight linalool, and 0.1 parts by weight alpha-ionone were compounded and mixed well to provide a flavor enhancing composition in accordance with the invention.

The flavor enhancing compositions provided in accordance with the invention can be used to enhance the flavors of comestible products such as mints, candy, taffy, toffee, hard candies, and chewing gum, as well as mouthwash, toothpaste, denture cleansers, dental floss, and the like.

Formulations, compositions, and processes for making such products are conventional and well known in the art. They are described, for example, in U.S. Pat. No. 4,929,508, issued May 29, 1990, the specification of which is incorporated herein by reference.

The following Examples 3–10 show exemplary uses of the flavor compositions of Examples 1 and 2. These examples are presented for purposes of illustration only and are not to be construed in a limiting sense.

EXAMPLE 3

Twenty-one and seventeen-hundreths (21.17) parts by weight gum base was melted in a mixing kettle with a sigma type blade. Sixteen (16) parts by weight corn syrup, 62 parts by weight sugar, 0.8 parts by weight flavor, between about 0.3 and 0.1 parts by weight of a flavor enhancer provided in accordance with either of Examples 1 or 2, and color to make up 100 parts by weight were added. The mixture was extruded, passed through sizing rollers, cut into pieces, conditioned to firmness, and wrapped. Accordingly, a sugared chewing gum having enhanced flavor was provided.

EXAMPLE 4

Twenty-three and nine-tenths (23.9) parts by weight gum base were melted and mixed in a mixing kettle with a sigma type blade. Forty-seven (47) parts by weight sorbitol, 22 parts by weight mannitol, 6 parts by weight glycerin, 0.07 parts by weight saccharin sodium, 1 part by weight flavor, between about 0.03 and 0.1 parts by weight of flavor enhancer provided in accordance with either of Examples 1 or 2, and color to make up 100 parts by weight were added. The mixture was extruded, passed through sizing rollers, cut into pieces, conditioned to firmness, and wrapped. Accordingly, a sugarless chewing gum having enhanced flavor was provided.

EXAMPLE 5

Three (3) parts by weight corn syrup was dissolved in water and used to wet 95.67 parts by weight sugar. The wet mix was passed through a screen and dried to approximately 0.5% moisture. The particle size of the dried mix was reduced by milling.

Three-tenths (0.3) parts by weight flavor, between about 0.03 and 0.1 parts by weight flavor enhancer provided in accordance with either of Examples 1 or 2, sufficient color to make up 100 parts by weight, and 1 part by weight magnesium stearate were added. The final mix was compressed into tablets using a tablet press. Accordingly, a compressed mint tablet having enhanced flavor was provided.

EXAMPLE 6

Ninety-eight and sixty-seven hundreths (98.67) parts by weight tabletting grade sorbitol were provided in a suitable mixer. Three-tenth (0.3) parts by weight flavor, between about 0.03 and 0.1 parts by weight flavor enhancer provided in accordance with either of Examples 1 or 2, sufficient color to make up 100 parts by weight, and 1 part by weight magnesium stearate were added. The final mix was compressed into tablets using a suitable tablet press. Accordingly, a sugarless mint tablet having enhanced flavor was provided.

EXAMPLE 7

Fifteen-hundreths (0.15) grams of benzoic acid, 0.09 grams of eucalyptol, 0.04 grams of menthol, 0.06 grams of methyl salicylate, 0.1 grams of Pluronic, 0.06 grams of thymol, between about 0.03 and 0.1 parts by weight of a flavor enhancer provided in accordance with either of Examples 1 or 2, and sufficient color were dissolved in 28 ml of alcohol. Sufficient water was added to make about 100 ml and the pH was adjusted to about 4.5 using a suitable acid or base. Additional water was added to make 100 ml. According, a mouthwash having enhanced flavor was provided.

EXAMPLE 8

Two-tenths (0.2) grams of benzoic acid, 0.09 grams of eucalyptol, 10 grams of glycerin, 0.04 grams of menthol, 0.06 grams of methyl salicylate, 0.4 grams of Pluronic, 0.06 grams of sodium saccharin, 0.2 grams of sodium benzoate, 0.2 grams of sodium lauryl sulfate, 0.06 grams of thymol, 0.01 grams of zinc chloride, between about 0.03 and 0.1 parts by weight flavor enhancer prepared in accordance with either of Examples 1 or 2, and sufficient color were dissolved in about 50 ml water. Additional water was added to make about 100 ml. The pH was adjusted to about 4.5 using a suitable acid or base. Accordingly, a non-alcoholic mouthwash having enhanced flavor was provided.

EXAMPLE 9

Two-tenths (0.2) parts by weight benzoate sodium, 0.8 parts by weight cellulose gum, 88.9 parts by weight dicalcium phosphate dihydrate, 1 part by weight flavor, 8 parts by weight glycerin, 0.05 parts by weight saccharin sodium, 0.2 parts by weight sodium lauryl sulfate, 0.76 parts by weight sodium monofluorophosphate, 0.06 parts by weight tetrasodium pyrophosphate, between about 0.03 and 0.1 parts by weight of a flavor enhancer provided in accordance with either of Examples 1 or 2, 0.005 parts by weight color, and sufficient water to make up 100 parts by weight were combined into a toothpaste. Accordingly, a toothpaste having enhanced flavor was provided.

EXAMPLE 10

Twenty-eight and two-hundreths (28.02) parts by weight potassium monopersulfate, 25 parts by weight sodium borate perhydrate, 25 parts by weight sodium carbonate, 0.5 parts by weight sodium lauryl sulfoacetate, 10 parts by weight sodium bicarbonate, 10 parts by weight citric acid, 0.75 parts by weight magnesium stearate, 0.2 parts by weight flavor, between about 0.03 and 0.1 parts by weight of a flavor enhancer provided in accordance with either of Examples 1 or 2, 0.5 parts by weight tetrasodium phosphate, and sufficient color to make up 100 parts by weight were combined and formed into an effervescent tablet for use as a denture cleanser. Accordingly, an effervescent denture cleansing tablet having enhanced flavor was provided.

Accordingly, it can be seen that an effective flavor enhancing composition containing benzyl benzoate and neryl acetate is provided in accordance with the invention. The flavor enhancing composition of the invention can be used to enhance the flavors of chewing gum, mints, mouthwash, toothpaste, denture cleansing compositions, and the like.

It is to be understood that the following claims are intended to cover all of the generic and specific features of the invention herein described and all statements of the scope of the invention which, as a matter of language, might be said to fall therebetween and, since certain changes may be made in the above-described composition without departing from the spirit and scope of the invention, it is intended that all matter contained in the above description shall be interpreted as illustrative and not in a limiting sense.

Particularly, it is to be understood that in said claims ingredients or compounds recited in the singular are intended to include compatible mixtures of such ingredients wherever the sense permits.

What is claimed is:

1. A flavor enhancing composition comprising:

between about 30% and 90% by weight benzyl benzoate; and, between about 3% and 15% by weight neryl acetate.

2. The flavor enhancing composition of claim 1 wherein the composition is spray dried on a suitable carrier.

3. The flavor enhancing composition of claim 2 wherein the carrier is selected from the group consisting of maltodextrin, modified food starch, gum acacia, dextrin, corn syrup sol ids, and mixtures thereof.

4. The flavor enhancing composition of claim 1 wherein the composition is a liquid in a suitable vehicle.

5. The flavor enhancing composition of claim 1 wherein the vehicle is selected from the group consisting of ethyl alcohol, propylene glycol, glycerol, hydrogenated oils, non-hydrogenated oils, food starches, and mixtures thereof.

6. The flavor enhancing composition of claim 1 wherein the composition further comprises a flavor enhancing agent selected from the group consisting of citronellyl acetate, geranyl acetate, geranyl propionate, linalool, alpha-ionone, 2,2,6-trimethyl-6-vinyl-tetra-hydropyran, citronella oil, and mixtures thereof.

7. The composition of claim 6 wherein the flavor enhancing agent is present in an amount between about 0.01% and 1% by weight of the composition.

8. A comestible product comprising a flavor enhancing agent including between about 30% and 90% by weight benzyl benzoate and between about 3% and 15% by weight neryl acetate in a suitable vehicle.

9. The comestible product of claim 8 wherein the vehicle is a chewing gum.

10. The comestible product of claim 9 wherein the vehicle is a mint.

11. The comestible product of claim 9 wherein the vehicle is a mouthwash.

12. The comestible product of claim 9 wherein the vehicle is a toothpaste.

13. The comestible product of claim 9 wherein the vehicle is an effervescent denture cleansing tablet.

* * * * *